(12) United States Patent
Patterson et al.

(10) Patent No.: US 6,545,048 B1
(45) Date of Patent: Apr. 8, 2003

(54) COMPOSITIONS AND METHODS OF TREATING CANCER USING COMPOSITIONS COMPRISING AN INHIBITOR OR ENDOTHELIN RECEPTOR ACTIVITY

(75) Inventors: Paul H. Patterson, Altadena, CA (US); Ronit Lahav, Venice, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/404,626

(22) Filed: Sep. 23, 1999

Related U.S. Application Data

(60) Provisional application No. 60/141,450, filed on Jun. 29, 1999.

(51) Int. Cl.$^7$ .............................................. A61K 31/195
(52) U.S. Cl. ............................ 514/561; 514/2; 514/564
(58) Field of Search .............................. 514/2, 561, 564

(56) References Cited

U.S. PATENT DOCUMENTS 5,550,110 A * 8/1996 Cody et al. .................... 514/17

FOREIGN PATENT DOCUMENTS

| DE | WO 98/41206 A1 | * | 9/1998 |
| WO | 98/41206 | | 9/1998 |
| WO | 00/36918 | | 6/2000 |

OTHER PUBLICATIONS

Janus et al., "ABT–627, endothelin–receptor antagonist, for advanced caner: Phase I pharmacokinetic results," Abstract to Proc. Amer. Canc. Res. Annual Meeting (04–1999), 40:90–91 Meeeting Info: 90$^{th}$ Annual Meeting American Association for Cancer.*
Nelson et al., Cancer Res., 56:663–668, Feb. 1996.
Ishikawa et al., Proc. Natl. Acad. Sci. USA, 91:4892–4896, May 1994.
Ohtani et al., Biochem. Biophys. Res. Commun., 234:526–430, 1997, Feb. 1996.
Seino et al., "Antitumor effect of locally produced CD95 ligand", Nature Med., 3(2):165–170 (Feb. 1997).
Yohn et al., "Human Melanoma Cells Express Functional Endothelin–1 Receptors," Biochem. Biophys. Res. Commun., 201(1):449–457 (May 1994).
Kikuchi et al., "Decreased ET$_B$ Receptor Expression in Human Metastatic Melanoma Cells," Biochem. Biophys. Res. Commun., 219:734–739 (1996).
Ohtani et al., "Bromodeoxyuridine–Induced Expression of Endothelin$_A$ in A375 Human Melanoma Cells," Biochem. Biophys. Res. Commun., 234:526–530 (1997).
Zhang et al., "Truncated human endothelin receptor A produced by alternative splicing and its expression in melanoma," Brit. J. Cancer, 78(9):1141–1146 (1988).
Okazawa et al., "Endothelin–induced Apoptosis of A375 Human Melanoma Cells," J. Biol. Chem., 273(20):12584–12592 (1998).
Hashimoto et al., "Endothelin ET$_B$ Receptor–Mediated Action on Systemic and Renal Hemodynamics and Urine Formation in Deoxycorticosterone Acetate–Salt–Induced Hypertensive Rats," Biol. Pharm. Bull., 21(8)800–804 (1998).
Lahav et al., "Endothelin 3 promotes neural crest cell proliferation and mediates a vast incearse in melanocyte number in culture, " PNAS, 93:3892–3897 (Apr. 1996).
Nelson et al., "Endothelin–1 Production and Decreased Endothelin B Receptor Expression in Advanced Prostate Cander," Cancer Res., 56:663–668 (Feb. 1996).
Bagnato et al., "Expression of Endothelin 1 and Endothelin A Receptor in Ovarian Carcinoma: Evidence for an Autocrine Role in Tumor Growth," Cancer Res., 59:720–727 (Feb. 1999).
Baynash et al., "Interaction of Endothelin–3 with Endothelin–B Receptor is Essential for Development of Epidermal Melanocytes and Enteric Neurons," Cell, 79:1277–1285 (Dec. 1994).
Ishikawa et al., "Biochemical and pharmacological profile of a potent and selectie endothelin B–receptor antagonists, BQ–799," Proc. Natl. Acad. Sci. USA, 91:4892–4896 (May 1994).
Hashimoto et al., "Endothelin ET$_B$Receptor–Mediated Action on Systemic and Renal Hemodynamics and Urine Formation in Deoxycorticosterone Acetate–Salt–Induced Hypertensive Rats," Biol. Pharm. Bull., 21:(8)800–804 (1998).
Itoh et al., "A Nove Endothelin ET$_A$ Receptor Antagonist, BQ–485, and Its Preventive Effect on Experimental Cerebral Vasospasm in Dogs," Biochem Biophys. Res Commun., 195(2):969–975 (Sep. 1993).
Hosoda et al., "Targeted and Natural (Piebald–Lethal) Mutations on Endothelin–B Receptor Gene Produce Megacolon Associated with Spotted Coat Color in Mice," Cell, 79:1267–1276 (Dec. 1994).
Puttenberger et al., "A Missense Mutation of the Endothelin–B Receptor Gene in Multigenic Hirshsprung's Disease," Cell, 79:1257–1266 (Dec. 1994).

(List continued on next page.)

Primary Examiner—Dwayne C. Jones
(74) Attorney, Agent, or Firm—Dorsey & Whitney LLP; Richard F. Trecartin; Nancy B. Capps

(57) ABSTRACT

Described herein are results which show that an endothelin receptor antagonist, BQ788, increases pigmentation and significantly reduces the viability of 7 human melanoma cell lines in culture. Moreover, it is described herein that administration of BQ788 significantly slows melanoma tumor growth in nude mice, including a complete growth arrest in half of the mice treated systemically. Thus, inhibitors of endothelin receptor activity are described herein as beneficial for the treatment of cancer.

16 Claims, 6 Drawing Sheets

OTHER PUBLICATIONS

Nelson, J.B., et al., "Identification of endothelin–1 in the pathophysiology of metastatic adenocarcinoma of the prostate," *Nature Medicine* 1(9):944–949 (Sep. 1995).

Kroodsma, J.M and Rabelink, A.J., "Endothelinen: mogelijk een niew farmacologish aangrijpingspunt bih hart–en vaatziekten, nierziekten en oncologishce aandoeningen," *Ned Tijdschr Geneeskd* (Sep. 1997) 141(38):1806–1810 (English translation also provided).

Endothelin Inhibitors: Exploring Novel Therapeutics, Investigation al Drugs Database Meeting Report, Washington, D.C. Jun. 7–8, 1999 (Jun. 25, 1999).

Boven, E., American Society of Clinical Oncology—$35^{th}$ Annual Meeting (Part I), Atlanta, GA, May 15–18, 1999, Investigation al Drugs Database Meeting Report (Sep. 13, 2001).

McKinnon, C.: American Society of Clinical Oncology—$35^{th}$ Annual Meeting (Part IV), Atlanta, GA, May 15–18, 1999, Investigation al Drugs Database Meeting Report (Sep. 13, 2001).

Adeniyi, A.: American Urological Association—$94^{th}$ Annual Meeting, Dallas, TX, May 1–6, 1999 Investigation al Drugs Database Meeting Report (Aug. 26, 1999).

Boven, E., "American Society of Clinical Oncology—$35^{th}$ Annual Meeting, May 15–18, 1999, Atlanta, GA, USA," *IDRUGS* 1999 2(7):617–619.

McKinnon, C.., "Topoisomerase inhibitors and other new agents" *IDRUGS* 1999 2(7):629–632.

Adeniyi, A., "American Urological Association–$94^{th}$ Annual Meeting, May 16, 1999, Dallas, USA" *IDRUGS* 1999 2(7):656–658.

Lahav et al. , "An endothelin receptor B antagonist inhibits growth and induces cell death in human melanoma cells in vitro and in vivo," *Proc. Natl. Acad. Sci. USA* 96:11496–11500 (Sep. 1999).

Giraldi et al., "Primary Tumor Growth and Formation of Spontaneous Lung Metastases in Mice Bearing Lewis Carcinoma Treated with Proteinase Inhibitors," *Anticancer Res* 4:221–224 (1984).

Tuerk et al., "Inhibition of growth of prostate cancer cell lines by endothelin receptor antagonists," *J. Urology* (Apr. 1999) 161(4 Suppl): 62 Meeting Info: 94th Annual Meeting of the American Urological Association (Abstract) from Database BIOSIS Online; Biosciences Information Service, Philadelphia, PA, USA.

Carducci et al., "Endothelin receptor antagonist, ABT–627, for prostate cancer: initial trial results," *J. Urology* (Apr. 1999) 161(4 Suppl): 176 Meeting Info: 94th Annual Meeting of the American Urological Association (Abstract) from Database BIOSIS Online; Biosciences Information Service, Philadelphia, PA, USA.

Carducci et al., "Phase I clinical results of ABT–627, an endothelin receptor antagonist, for refractory adenocarcinomas," Proc. Amer. Assoc. for Cancer Res. Annual Meeting (Mar. 1999), 40:91 Meeting Info: 90th Annual Meeting of the American Association for Cancer Research (Abstract) from Database BIOSIS Online; Biosciences Information Service, Philadelphia, PA, USA.

Kroodsma and Rabelink, "Endothelins: Possibly a new approach to pharmacotherapy of cardiovascular diseases, renal diseases and oncological conditions," *Ned Tijdschr Geneeskd* (Sep. 1997) 141(38):1806–1810 (English Abstract).

Moraitis et al., "Endothelin Expression and Responsiveness in Human Ovarian Carcinoma Cell Lines," *Eur. J. Cancer* 33(4):661–668 (1997).

Janus et al., "ABT–627, endothelin–receptor antagonist, for advaned cancer: Phase I pharmacokinetic results," Proc. Amer. Assoc. for Cancer Res. Annual Meeting (Mar. 1999), 40:90–91 Meeting Info: 90th Annual Meeting of the American Association for Cancer Research (Abstract).

* cited by examiner

FIG._1A
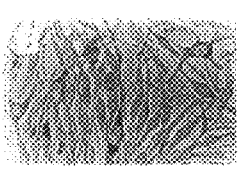
FIG._1B
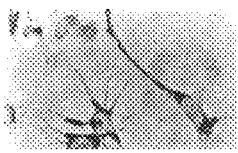
FIG._1C
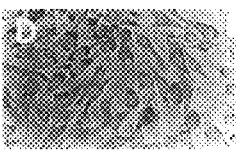
FIG._1D
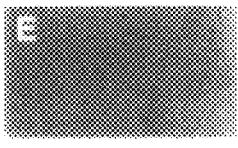
FIG._1E
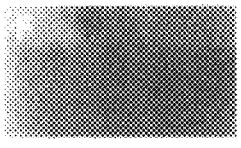
FIG._1F
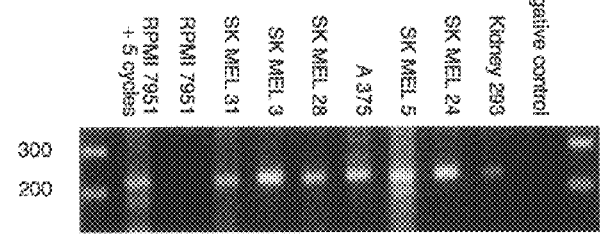
FIG._3A
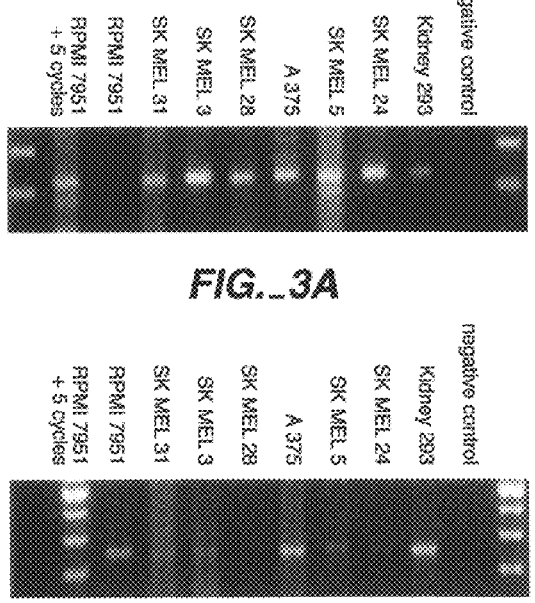
FIG._3B

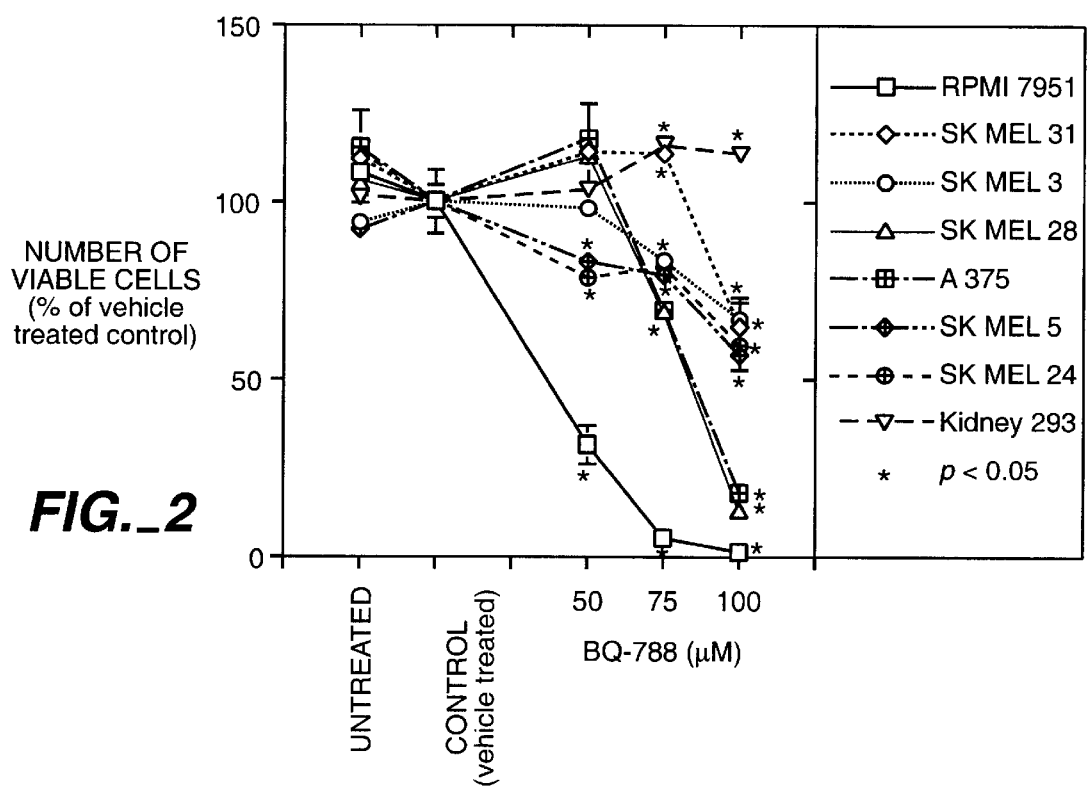
FIG._2
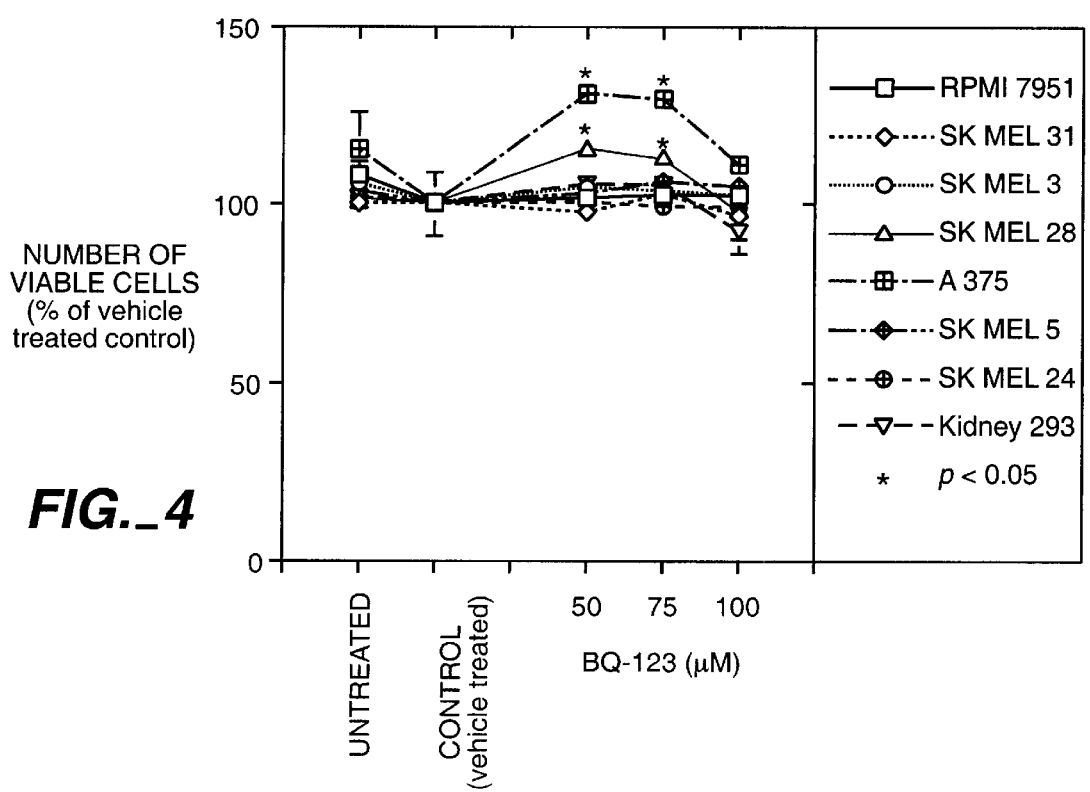
FIG._4

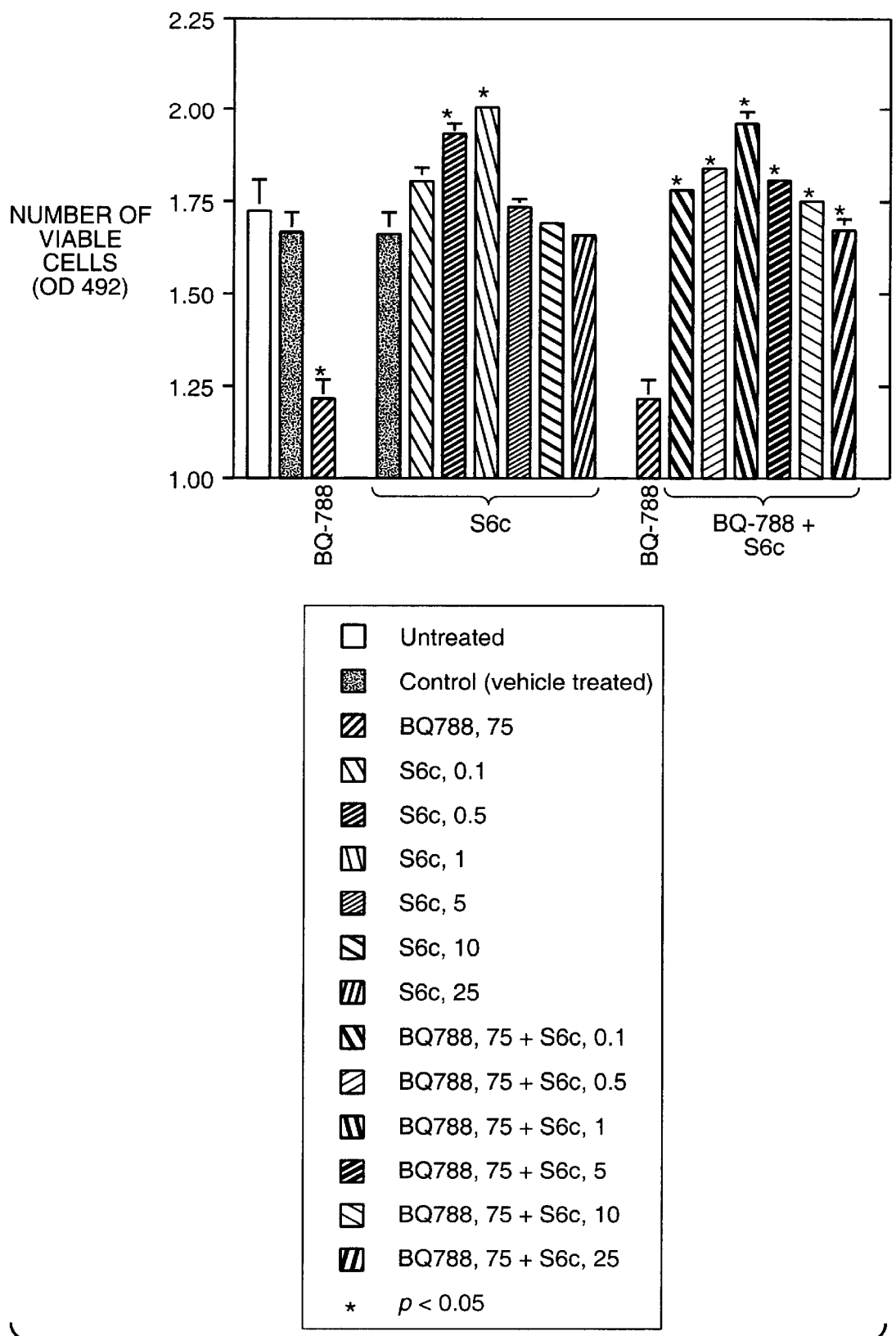
FIG._5

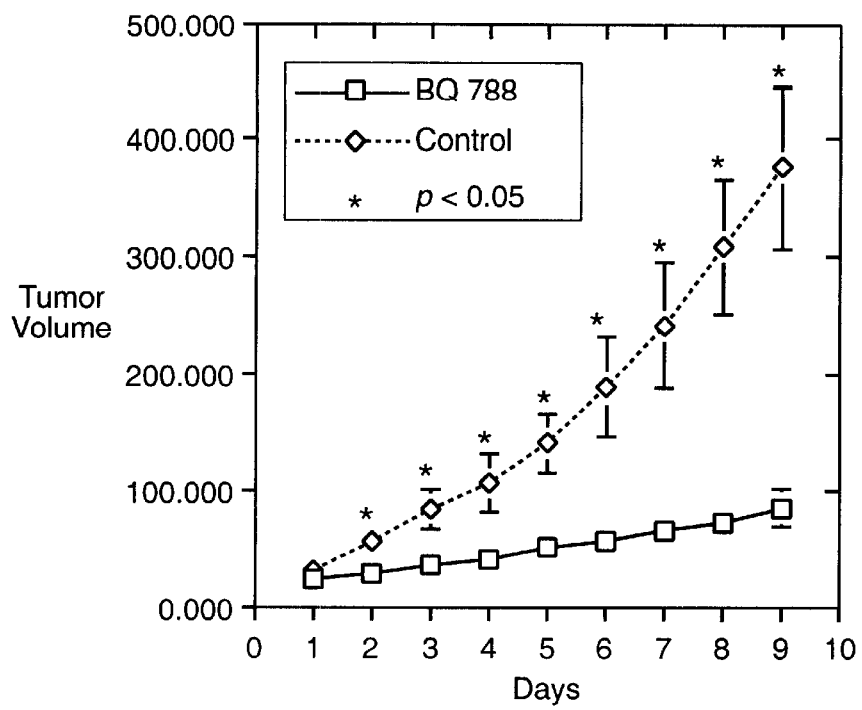
FIG._6
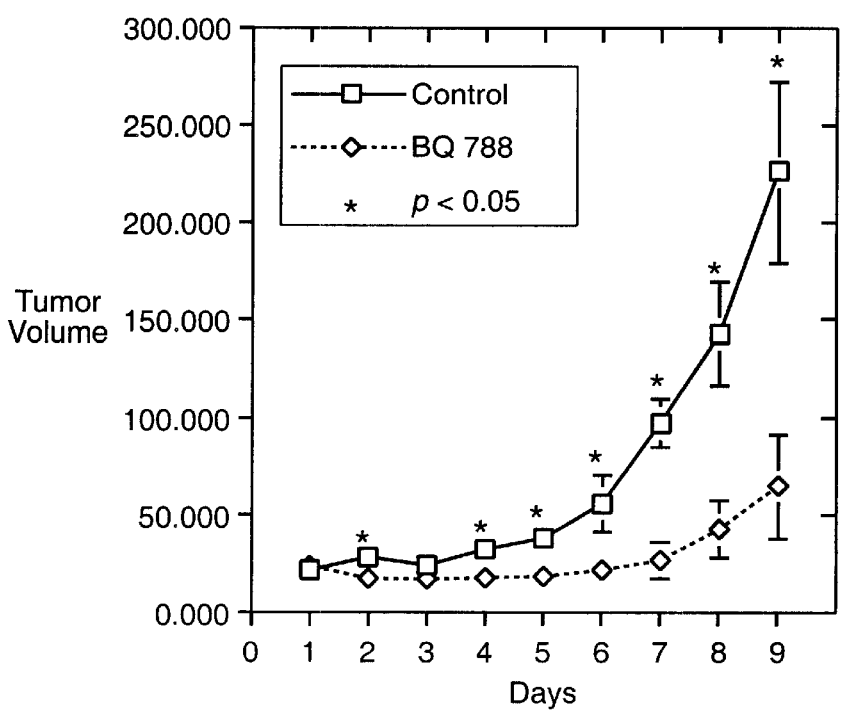
FIG._7A

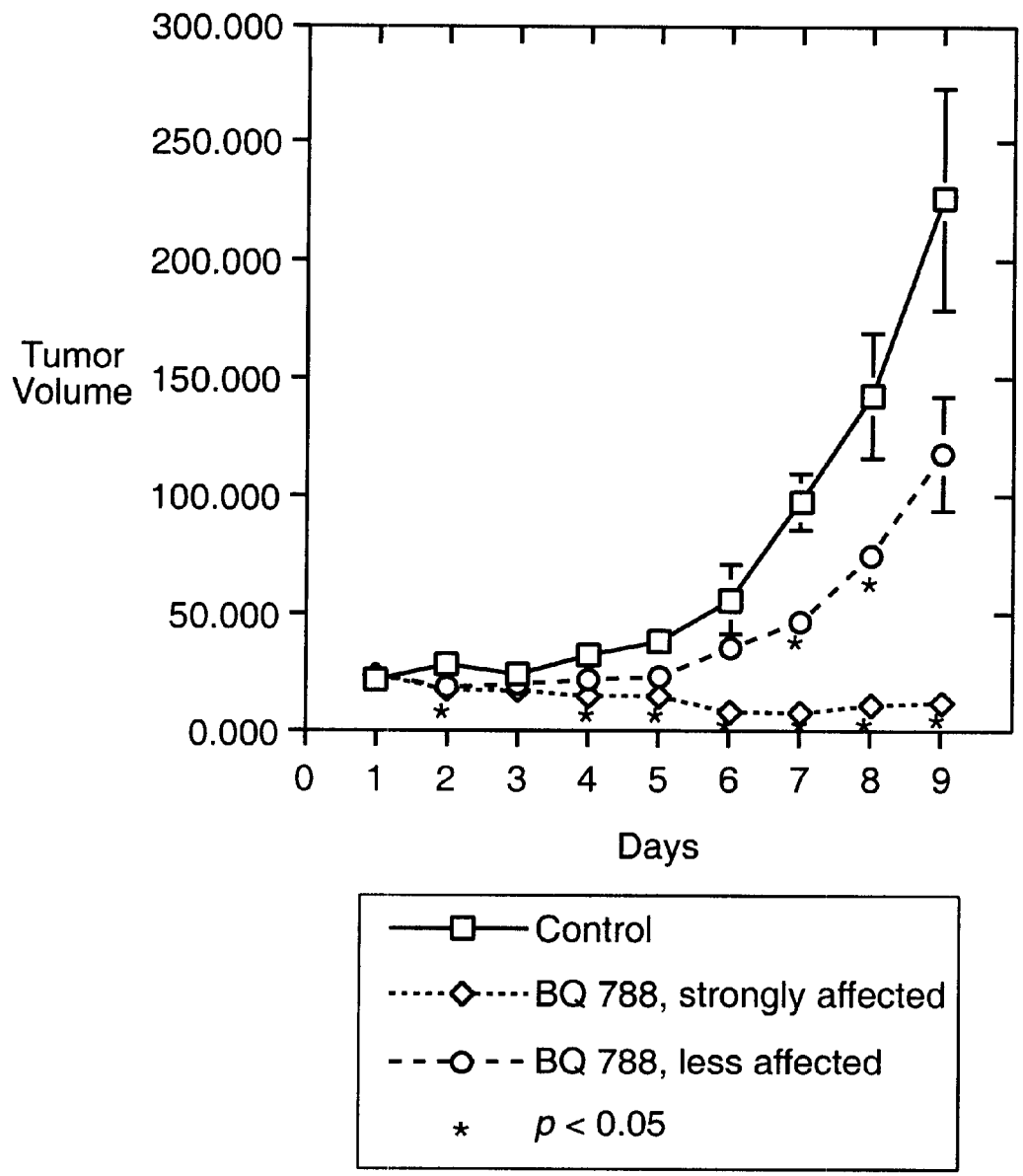
FIG._7B

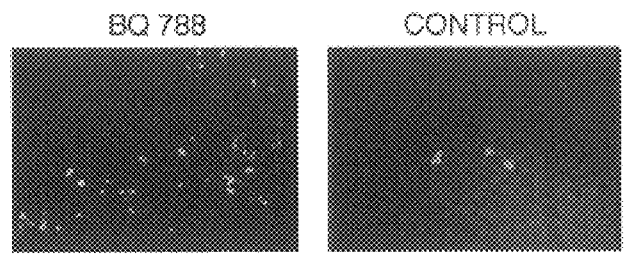
FIG._8A  FIG._8E
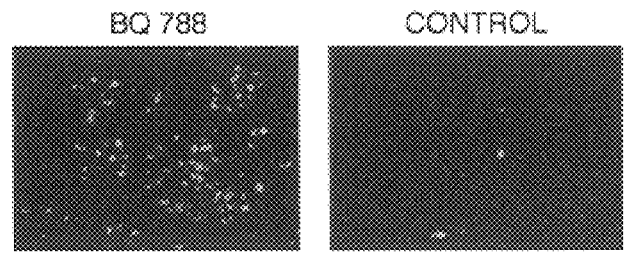
FIG._8B  FIG._8F
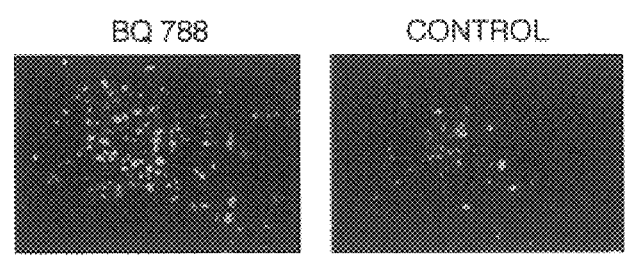
FIG._8C  FIG._8G
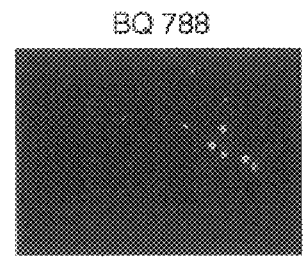
FIG._8D

COMPOSITIONS AND METHODS OF TREATING CANCER USING COMPOSITIONS COMPRISING AN INHIBITOR OR ENDOTHELIN RECEPTOR ACTIVITY

This Application claims the benefit of Provisional Application No. 60/141,450 field Jun. 29, 1999.

One-third of all individuals in the United States alone will develop cancer. Although the five year survival rate has risen dramatically nearly fifty percent as a result of progress in early diagnosis and therapy, cancer still remains second only to cardiac disease as a cause of death in the United States. Twenty percent of Americans die from cancer, half due to lung, breast, and colon-rectal cancer. Moreover, skin cancer remains a health hazard.

Designing effective treatments for patients with cancer has represented a major challenge. The current regimen of surgical resection, external beam radiation therapy, and/or systemic chemotherapy has been partially successful in some kinds of malignancies, but has not produced satisfactory results in others. One approach to treating cancer has been to induce apoptosis (cell death) of targeted tumor cells; therefore, mechanisms inducing apoptosis are of interest. One such mechanism has been reported where the Fas ligand, (FasL) (also known as CD95L and APO-IL), a cell surface molecule belonging to the tumor necrosis factor family, induces apoptosis of Fas-bearing tumor cells. Seino, et al., *Nature Med.,* 3(2):165 (1997).

In another approach, cancer cell lines have been characterized. For example, it has been reported that all human melanoma lines tested in a number of studies express endothelin B-receptor (ETRB) (Yohn, et al., *Biochem. Biophys. Res. Commun.,* 201:449–57 (1994); Kikuchi, et al., *Biochem. Biophys. Res. Commun.,* 219:734–9 (1996); Ohtani, et al., *Biochem. Biophys. Res. Commun.,* 234:526–30 (1997); Zhang, et al., *Brit. J. Cancer,* 78:1141–6 (1988)); moreover, expression is correlated with their differentiation state. Increased endothelin A-receptor (ETRA) expression is associated with induced differentiation of A375 melanoma cells, while they predominantly express ETRB in their malignant state (Ohtani, et al., *Biochem. Biophys. Res. Commun.,* 234:526–30 (1997)). Unfortunately, the roles of endothelin receptors (ETRs) is not clear from previous studies. While one report indicates that endothelin-1 (ET1), acting through the ETRB, mediates mitogenic and chemokinetic effects on melanoma cells (Yohn, et al., *Biochem. Biophys. Res. Commun.,* 201:449–57 (1994)), another report suggests other mechanisms for ET1 (Okazawa, et al., *J. Biol. Chem.,* 273:12584–92 (1998)). Moreover, at least in one study, the focus of ETRB has been in regards to hypertension (Hashimoto, et al., *Biol. Pharm. Bull.,* 21(8):800–804 (1998)). Additionally, endothelin-3 (ET3) has been reported on, however, many such reports are regarding developing non-malignant (normal) cells (Lahau, et al., *PNAS,* 93:3892–7 (1996)).

Studies have reported on ETRA and ET1 activity in regards to malignant cells, however, these studies were performed in vitro. For example, see Nelson, et al., Cancer Res., 56:663–8 (1996).

Therefore, there remains a need to identify compounds which can be used in vivo to treat diseases such as cancer. In particular, there is a need to be able to selectively target malignant cells and induce cell death.

SUMMARY OF THE INVENTION

The present invention provides compositions and methods of treatment. In one aspect, a method of treating cancer is provided. In one embodiment, the method comprises administering to an individual in need of treatment for cancer, an inhibitor of an endothelin receptor activity, in a therapeutically effective amount. Preferably, the receptor is an endothelin B- or A-receptor. Administration can occur by a number of methods known in the art including by administration directly to the tumor site, or preferably, administration is systemic.

In one aspect, any kind of cancer is treated. Preferably, the cancer is skin, ovarian or prostrate cancer. In another preferred embodiment, the cancer is in a metastatic state.

In one embodiment, the inhibitor is an endothelin B-receptor or A-receptor antagonist. In a preferred embodiment, the inhibitor is BQ788 or a derivative thereof. In another preferred embodiment, the inhibitor is an antisense molecule to an endothelin receptor nucleic acid or an endothelin receptor agonist nucleic acid.

In another aspect, the invention provides a method for reducing abnormal proliferation or inducing differentiation of a cell. In a preferred embodiment, said cell comprises an endothelin receptor, preferably, an endothelin B-receptor. In one embodiment, the method comprising administering an inhibitor to an endothelin receptor to said cell in an amount for reducing proliferation or inducing differentiation. In yet another embodiment, a method for inducing apoptosis in a cell is provided. One method comprises administering an inhibitor to an endothelinreceptor, preferably an endothelin B-receptor, to said cell in an amount for inducing apoptosis. Preferably, the cell is a cancer cell.

Also provided herein is a method for screening for a bioactive agent capable of interfering with the binding of an endothelin receptor, preferably an endothelin B-receptor, and a ligand. In a preferred embodiment, the method comprises combining an endothelin receptor, a candidate bioactive agent and a ligand, and determining the binding of said receptor and said ligand. Preferably, the ligand is selected from the group consisting of endothelin 3, S6c, BQ-3020, and BQ-788, In another aspect, a method for delivering a substance to a cancerous cell in an individual is provided. The method comprises conjugating a substance to BQ788 or a derivative thereof to form a conjugate and administering said conjugate to said individual.

BRIEF DESCRIPTION OF THE FIGURES

FIGS. 1A–1F show pictures indicating that the ETRB antagonist BQ788 induces morphological changes in cultured melanoma cells. Cells were cultured for 4 days with 100 $\mu$M BQ788 (FIGS. A, C, and E) or with vehicle (FIGS. B, D, and F). The cell lines were melanoma line SK-MEL 28 (FIGS. A and B), melanoma line SK-MEL 5 (FIGS. C and D), and kidney 293 (FIGS. E and F). The drug-treated melanoma cells have a different shape and accumulation of black pigment. Pictures were taken with bright field optics at 40×magnification.

FIG. 2 is a graph indicating that BQ788 reduces the number of viable cells in cultured melanoma but not kidney cells. Cells were cultured in the presence of BQ788 or vehicle or with no treatment for 4 days. Three wells of each condition were subjected to the MTS assay. The means were calculated and plotted as percent of the vehicle-treated value, +S.E.M. P values were calculated using that test for absolute values. The experiment was repeated 3 times, each yielding similar results.

FIGS. 3A and 3B show pictures of gels showing RT-PCR results revealing the expression of ETRB and ETRA mRNA in various cells lines. Bands corresponding to ETRB (FIG. 3A) (220 bp) and ETRA (FIG. 3B) (352 bp) mRNAs were obtained using published primer sequences and protocols (21).

FIG. 4 is a graph indicating that the selective ETRA antagonist BQ123 does not reduce the number of viable cells in cultured melanoma cells. Conditions and presentation are as described for the BQ788 experiment shown in FIG. 2.

FIG. 5 is a graph indicating that the ETRB-selective agonist sarafotoxin 6c (S6c), can abrogate the effects of BQ788 on melanoma cells. In experiments similar to those illustrated in FIG. 2, S6c was tested for its effects on cultured A375 cells, alone or in combination with BQ788, at various concentrations. The ETRB agonist S6c stimulates cell growth and can block the inhibitory effects of the ETRB antagonist.

FIG. 6 is a graph indicating that intra-tumor injection of BQ788 inhibits melanoma tumor growth in nude mice. Nude mice (nu/nu, BALB/c background) were implanted with grafts of A375 cells subcutaneously on the flank. After the tumors had reached approximately 4 mm in diameter they were injected daily with BQ788 for 9 days. Perpendicular tumor diameters were measured daily to estimate tumor volume. Controls were injected on the same schedule with vehicle. Data from 3 experiments utilizing 10 BQ788-treated mice and 8-vehicle treated mice were pooled. P values were calculated using t test. Similar conclusions come from measuring tumor weights.

FIGS. 7A and 7B are graphs indicating that systemic administration of BQ788 inhibits melanoma tumor growth in nude mice. The experiment was similar to that described in FIG. 6, except that the drug and vehicle were injected daily i.p. In FIG. 7A, the data for the 6 BQ788-treated mice were pooled. In FIG. 7B, separate curves are drawn for the data from the 3 mice in which BQ788 slowed tumor growth, and for the data from the 3 mice in which BQ788 caused the tumors to regress.

FIGS. 8A–8G are photographs showing TUNEL staining of tumors indicating that BQ788 induces apoptosis. FIGS. 8A–8D show representative sections from 4 tumors from BQ788 injected mice and FIGS. 8E–8G show tumors from vehicle-injected mice. TUNEL-positive cells are comparatively greater in the drug treated animals, indicating enhanced apoptosis. The magnification is 20×.

DETAILED DESCRIPTION OF THE INVENTION

Provided herein are compositions which are specific for abnormally proliferating cells. Inhibition of the abnormal proliferation of cells is useful in treating a number of disorders such as cancer, autoimmune disease, arthritis, inflammatory bowel disease, proliferation induced after medical procedures, and many other instances. In particular, provided herein are methods of treating disorders requiring the inhibition of uncontrolled cell proliferation which are sensitive, specific and which have limited side effects.

In one embodiment, methods of treating hyperproliferative disorders and disease states requiring inhibition of cellular proliferation are provided herein. The disorder or disease state can be, but is not limited to cancer, autoimmune disease, arthritis, graft rejection, inflammatory bowel disease, proliferation induced after medical procedures, including, but not limited to, surgery, angioplasty, and the like. Thus, in one embodiment, the invention herein includes application to cells or individuals afflicted with any one of these disorders or disease states.

In a preferred embodiment, a method of treating cancer is provided. In some cases, the treatment of cancer may include the treatment of solid tumors or the treatment of metastasis. Metastasis is the form of cancer wherein the transformed or malignant cells are traveling and spreading the cancer from one site to another. The cancer can be of the skin, breast, brain, cervical carcinomas, testicular carcinomas, etc. More particularly, cancers may include, but are not limited to the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), neuroblastoma, pheochromocytoma, paraganlioma, meningioma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia. More preferably, the cancer is skin cancer. Skin cancer includes malignant melanoma, basal cell carcinoma, squamous cell carcinoma, Karposi's sarcoma, moles dysplastic nevi, lipoma, angioma, dermatofibroma, keloids, and psoriasis. Most preferably, the cancer is malignant melanoma. In yet another preferred embodiment, the cancer is metastatic melanoma. The term "cancerous cell" as provided herein, includes a cell afflicted by any one of the cancerous conditions provided herein. In another embodiment, the methods are for the treatment of benign overgrowth of melanocytes, glia, prostate hyperplasia, and polycystic kidney disease.

The individual, or patient, is generally a human subject, although as will be appreciated by those in the art, the patient may be animal as well. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

In one aspect, the method provided herein includes administering to an individual or a cell, an inhibitor of endothelin receptor (ETR) activity. ETR activity includes activities which are induced by agonists to an endothelin receptor. Endothelin receptors include the A- and B- receptors. Agonists of an ETR include ET1, ET2, ET3, and S6c. An ETR agonist as defined herein includes the ability enhance proliferation and/or delay differentiation.

In one embodiment an inhibitor of ETR activity as defined herein inhibits cancerous growth, or reduces proliferation, by at least 30%, more preferably 40%, more preferably 50%, more preferably 70%, more preferably 90%, and most preferably by at least 95%. In a preferred embodiment, the ETRB inhibitor causes tumor regression by at least 30%, more preferably 40%, more preferably 50%, more preferably 70%, more preferably 90%, and most preferably by at least 95%. The determination of inhibition or regression can be made by comparing the effect with treatment as described herein, compared to a control sample wherein treatment, for example, an inhibitor of the endothelin receptor, is not provided. In some cases, the control sample may have a tumor which grows to twice, three times, or four times the volume of the tissue being treated in accordance with the methods as described herein. In a preferred embodiment, treated tumors grow at least six times slower than controls. In one embodiment, an ETR activity inhibitor has ETR inhibitor activity. ETR inhibitor activity includes one or more of the following characteristics: inhibits cancerous growth, regresses cancer growth, induces apoptosis preferably in a cancerous cell, induces differentiation preferably in a cancerous cell, induces pigmentation preferably in a cancerous cell, antagonizes ET3, ET2 and/or ET1, binds to an ETR preferably selectively, and antagonizes S6c. Any combination of these characteristics including all or one or more with one or more exclusions is provided herein.

An ETR activity inhibitor, or an ETR inhibitor, as described herein includes BQ788 ard other compounds which are ETR inhibitors which have ETR inhibitor bioactivity. Preferably, the ETR inhibitor is an ETRB inhibitor. BQ788 (N-cis-2,6-dimethylpiperidinocarbonyl-L-γ-methylleucyl-D-1-methoxycarbonyltrptophanyl-D-norleucine has been previously described, e.g., Ishikawa, et al., PNAS, 91:4892–4896 (1994). Derivatives of BQ788 as used herein are functionally equivalent to BQ788 in that they have ETR, preferably ETRB, inhibitor activity. Other ETRB inhibitors include but are not limited to IRL1083, RES7011, RES7013, PD142983, and IRL2500.

In one embodiment, the ETR inhibitor is an ETRA inhibitor. ETA inhibitors include but are not limited to LU135252, BQ485, BQ123, FR139317, BE18257B, JKC301, JKC302, BQ610, PD156707, A127722, R061-1790, TBC11251, FR139317, S0139, A127722, SB234551, A192621, ABT627, A216546, PD155080, BMS182874, 97139, LU127043, and IRL1620.

In another embodiment, the ETR inhibitor binds to more than one ETR. Thus in one embodiment the ETR inhibitor is selected from the group consisting of LU302872, TAK044, PD142893, PD145065, BE18257A/W7338A, Bosentan (RO47-0203), SB217242, R0468443, SB209670, Tnieno [2,3-d]pyrimidine-3-aceticacids, R0610612, R0462005, PD156252, A182086, L744453, and L754142.

In another aspect of the invention, the ETR inhibitor is an antisense molecule to the nucleic acid encoding an ETR or an ETR native ligand such as ET1, ET2, or ET3. Antisense molecules include oligonucleotides comprising a singe-stranded nucleic acid sequence (either RNA or DNA) capable of binding to target receptor or ligand mRNA (sense) or DNA (antisense) sequences. Antisense or sense oligonucleotides, according to the present invention, comprise a fragment of the coding region of the receptor or ligand. Such a fragment generally comprises at least about 14 nucleotides, preferably from about 14 to 30 nucleotides. The ability to derive an antisense or a sense oligonucleotide, based upon a cDNA sequence encoding a given protein (previously described in the art) is described in, for example, Stein, et al., Cancer Res., 48:2659, (1988) and van der Krol, et al., Bio Techniques, 6:958 (1988). Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

In another aspect the ETR inhibitor is an inhibitor of the endothelin converting enzyme (ECE) which processes endothelin precursors. ECE inhibitors include but are not limited to CGS26303 and phosphoramidon. ECE antisense molecules can also be used Compositions which inhibit growth factor receptors in the same family as ETRB are also provided herein for methods of treatment. In particular, such compositions can be used for treating ovarian and prostate cancers.

In one embodiment, the inhibitor to the endothelin B-receptor is administered to a cell or individual prior to the development of the targeted disorder or disease. For example, a person at risk for a disorder or disease state as described herein may be treated with a composition comprising an inhibitor to the endothelin B-receptor to prevent or inhibit the development of the disorder or disease state. It is understood that the compositions provided herein are specific for abnormal or diseased cells, and do not have an inhibitory affect on normal, for example, non-malignant cells. Thus, the compositions can be administered to the cells prior to the disease state, but are effective after the disease state is induced.

In a preferred embodiment for each of the methods provided herein, the inhibitor as described herein is administered to a cell, preferably comprising an endothelin receptor, preferably an endothelin B-receptor. Endothelin B-receptors are localized at least to the endothelium and nonvascular tissues such as the liver, kidney and brain. The receptors are also located in certain vascular smooth muscle tissues. In a preferred embodiment, the endothelin B-receptor is expressed, but at a comparatively low level compared to expansion levels in other malignant cells. Thus, in one embodiment, relatively low levels of ETRB mRNA in a malignant cell provides a positive prognosis.

In another aspect of the present invention, a method for inducing differentiation in a cell is provided. Identification of differentiation can be determined through standard techniques in the art, including by identification of morphologic changes. In a preferred embodiment, the cell comprises an endothelin receptor, preferably an endothelin B-receptor. In another preferred embodiment, the cell is malignant. Most preferably, the cell is afflicted with skin cancer.

In a further embodiment, a method for inducing apoptosis in a cell is provided. The method for inducing apoptosis comprises administering an inhibitor to an endothelin receptor, preferably an endothelin B-receptor, to said cell in an amount for inducing apoptosis. In a preferred embodiment, the inhibitor is specific for an ETR, preferably an ETRB. More preferably, the inhibitor is BA788 or a BA788 derivative. In one embodiment, the inhibitor is exclusive of endothelin-1 (ET-1). A characteristic feature of apoptosis is activation of a cascade of cytoplasmic proteases that results in the cleavage of selected target proteins. Preferably, the cell is malignant. Most preferably, the cell is afflicted with skin cancer. Standard kits for identifying cells undergoing apoptosis, for example, the TUNEL method, are known in the art. Additionally, apoptosis can be identified by a significant increase in hypodiploid cells, chromatin condensation and/or DNA fragmentation.

In another embodiment, a method for screening for a bioactive agent capable of interfering with the binding of an endothelin receptor, preferably an endothelin B-receptor, and a ligand is provided. A ligand is any compound or composition which bonds to the receptor. Preferably, the ligand is an agonist or an antagonist. Most preferably, the method screens for interference between an agonist and the receptor. An agonist induces, increases or maintains ETR activity whereas an antagonist inhibits ETR activity.

In a preferred embodiment, identification of effects of an ETR inhibitor on a cell permits the design of drug screening assays for compounds that bind or interfere with the binding to ETR and for compounds which modulate ETR activity.

In a preferred embodiment, the methods comprise combining an ETR ligand, preferably an ETR inhibitor or agonist and a candidate bioactive agent, and determining the binding of the ETR and ETR ligand. In a preferred embodiment, an agonist is utilized. Preferably, the ETR is an ETRB. Wherein the binding is changed in the presence of the candidate bioactive agent, the candidate bioactive agent is identified as an agent which interferes in binding between an ETR and an ETR ligand. Preferably, the ETRB ligand is an agonist including ET3 or S6c. In other embodiments, further discussed below, bioactivity is determined.

The term "candidate bioactive agent" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowski, et al., *Angew. Chem. Intl. Ed. English*, 30:423 (1991); Letsinger, et al., *J. Am. Chem. Soc.*, 110:4470 (1988); Letsinger, et al., *Nucleoside & Nucleotide*, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev., (*1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature. Small molecules are particularly preferred. Small molecules are usually less than about 800 D, more preferably, less than 500 D, and more preferably, less than 200 D.

In another preferred embodiment, compounds or compositions with ETR activity, as described above, are identified through screening. ETRB activity includes one or more of the following characteristics: binding to ETRB, preferably selectively, inducing differentiation, inducing pigmentation, inducing proliferation, and inducing apoptosis. In a preferred embodiment, ETRB activity includes at least one of inducing differentiation, inducing pigmentation, inducing proliferation, and inducing apoptosis. More preferably, binding ETRB and at least one other of said characteristics identifies an agent which modulates ETRB activity.

Generally, in a preferred embodiment of the methods herein, for example for binding assays, an ETR, (for convenience, ETRB is used for illustration) or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the ETRB is bound to the support, and a candidate bioactive agent is added to the assay. Alternatively, the candidate agent is bound to the support and the ETRB is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled invitro protein-protein binding assays, electrophoretic mobility shift assays, immunoassays for protein binding, functional assays (phosphorylation assays, etc.) and the like.

The determination of the binding of the candidate bioactive agent to the ETRB may be done in a number of ways. In a preferred embodiment, the candidate bioactive agent is labeled, and binding determined directly. For example, this may be done by attaching all or a portion of the ETRB to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}I$, or with fluorophores. Alternatively, more than one component may be labeled with different labels; using $^{125}I$ for the proteins, for example, and a fluorophor for the candidate agents.

In a preferred embodiment, the methods herein include the use of competitive binding assays. In this embodiment, the competitor is a binding moiety known to bind to the target molecule (i.e. ETRB), such as an antibody, peptide, binding partner, ligand, etc. In a preferred embodiment, the competitor competes against an agonist such as ET3 or S6c. Most preferably, further assays are performed to identify the candidate agent as an antagonist. Under certain circumstances, there may be competitive binding as between the bioactive agent and the binding moiety, with the binding moiety displacing the bioactive agent. This assay can be used to determine candidate agents which interfere with binding between ETRBs and endothelin 3, S6c, BQ-3020, or BQ-788. "Interference of binding" as used herein means that native binding of the ETRB differs in the presence of the candidate agent. The binding can be eliminated or can be with a reduced affinity. Therefore, in one embodiment, interference is caused by, for example, a conformation change, rather than direct competition for the native binding site. The described methods can also be performed using ETRA.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the ETRB and thus is capable of binding to, and potentially modulating, the activity of the ETRB. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the ETRB with a higher affinity. Thus, if the candidate bioactive agent is labeled, the presence of the label on the support, coupled with a lack of competitor binding, may indicate that the candidate agent is capable of binding to the ETRB.

In a preferred embodiment, the methods comprise differential screening to identity bioactive agents that are capable of modulating the activity of ETRB. Such assays can be done with the ETRB or cells comprising said ETRB. In one embodiment, the methods comprise combining an ETRB and a competitor in a first sample. A second sample comprises a candidate bioactive agent, an ETRB and a competitor. The binding of the competitor is determined for both samples, and a change, or difference in binding between the two samples indicates the presence of an agent capable of binding to the ETRB and potentially modulating its activity. That is, if the binding of the competitor is different in the second sample relative to the first sample, the agent is capable of binding to the ETRB.

Alternatively, a preferred embodiment utilizes differential screening to identify drug candidates that bind to the native ETR, but cannot bind to modified ETRs. The structure of the ETR may be modeled, and used in rational drug design to synthesize agents that interact with that site. Drug candidates that affect ETR bioactivity are also identified by screening drugs for the ability to either enhance or reduce the activity of the protein.

In one embodiment herein where BQ788 is added and tumor growth is inhibited, the binding site to which BQ788 binds is identified and isolated.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc. which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of ETR may also be done. In a preferred embodiment, methods for screening for a bioactive agent capable of modulating the activity of ETR comprise the steps of adding a candidate bioactive agent to a sample of a ETR (or cells comprising a ETR) and determining an alteration in the biological activity of the ETR. Preferably, the ETR is ETRB. In a preferred method, this is done with agents already identified as binding to ETR; in this embodiment, the bioactivity change, if any, that is determined is selected from inducing proliferation, differentiation, and apoptosis. "Modulating the activity of a ETR" includes an increase in activity, a decrease in activity, or a change in the type or kind of activity present. Thus, in a preferred embodiment, the candidate agent should both bind to ETR (although this may not be necessary), and alter its biological or biochemical activity as defined herein. The methods include both in vitro screening methods, as are generally outlined above, and in vivo screening of cells for alterations in the activity of ETR.

In one embodiment, the methods comprise adding a candidate bioactive agent, as defined above, to a cell comprising ETRs. Preferred cell types include almost any cell. In a preferred embodiment, the cell is cancerous, or exposed to cancer causing agents after the bioactive agent is present. The cells can contain a recombinant nucleic acid that encodes an ETR, or native ETR. In a preferred embodiment, a library of candidate agents are tested on a plurality of cells.

The measurements can be determined wherein all of the conditions are the same for each measurement, or under various conditions, with or without bioactive agents, or at different stages of a disease state such as cancer. For example, a measurement can be determined in a cell or cell population wherein a candidate bioactive agent is present and wherein the candidate bioactive agent is absent. For another example, the cells may be evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In yet another example, the measurements of bioactivity are taken wherein the conditions are the same, and the alterations are between one cell or cell population and another cell or cell population.

By a "population of cells" or "library of cells" herein is meant at least two cells, with at least about $10^3$ being preferred, at least about $10^5$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc.

The compositions described herein, including ETR modulators, preferably inhibitors including those identified as such through the assays provided herein, can be combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96. The term "therapeutically effective" amount as used herein refers to the amount needed to perform the particular treatment such as, for example, cancer. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In a preferred embodiment, the disorder is present. In a preferred embodiment, the life of a cell or an individual is prolonged due to the methods described herein.

The compositions provided herein may be administered in a physiologically acceptable carrier to a host, as previously described. Preferred methods of administration include systemic or direct administration to a tumor cavity. In one method sustained release vehicles are utilized. The compositions may be administered in conjunction with other compositions for treatment, including but not limited to chemotherapeutics and/or radiation or with regulators thereof.

Antisense or sense oligonucleotides may be introduced into a cell by any gene transfer method. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

In a further aspect of the present invention, a method of targeting cancerous cells is provided. In one embodiment, a compound or composition to be delivered to a cell is conjugated to BQ788 or a derivative thereof which is specific for the ETR. Preferably, the individual or sample of cells contains malignant cells expressing ETR. The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety. Moreover, all sequences displayed, cited by reference or accession number in the references are incorporated by reference herein.

EXAMPLE 1

BQ788 Induces Differentiation and Apoptosis in Cancerous Cells and Inhibits Cancer in Vivo Methods Cell culture. Human melanoma cell lines were obtained from the American Tissue Culture Collection (ATCC) and were cultured with Dulbecco's Eagle medium (ATCC), containing 10% fetal calf serum, glutamine (Gibco) and antibiotics (concentration; Pen-Strep mix, Gibco) in a humidified incubator with 5% CO2 at 37° C. BQ788 and BQ123 (Calbiochem) were dissolved in 2% polyoxythylene (60) hydrogenated castor oil (HCO60; Nikko Chemicals). Cells were cultured in 96 well ELISA plates. For the cell viability/cell number assay, the day after plating, inhibitor or vehicle was added ard the cultures incubated for 4 days. The MTS assay was used to quantify cells by measuring OD at 492 $\mu$m (Promega).

Reverse transcription-PCR analysis. Total RNA was isolated from each cell line using an RNA isolation kit (Promega). The cDNA was prepared from 10 $\mu$g total RNA using MMLV Reverse Transcriptase. Two $\mu$g of cDNA were used for each PCR reaction. Primers and conditions were used as previously described (Hamroun, et al., J. Cardiovasc, Pharmacol., 26(3):S156–8 (1995)).

Immunohistochemistry. Tumors were frozen on dry ice, cut on a cryostat into 20 $\mu$m sections, and stored at –80° C. Sections were rinsed in calcium and magnesium-free phosphate buffered saline (PBS), fixed in 4% paraformaldehyde for 1 hour at room temperature, blocked with 2% rabbit serum and incubated with primary antibody overnight at 4° C. After washing in PBS sections were incubated with a biotinylated secondary antibody, and staining developed using the Elite ABC kit (Vector Laboratories, CA). The primary antibodies used in this study were monoclonal rat anti-mouse CD31 (platelet endothelial cell adhesion molecule) and rat anti-mouse CD45 (leukocyte common antigen found on all cells of hematopoietic origin, except erythrocytes) (Pharmagen, San Diego, Calif.). A cell death kit was used for TUNEL staining (Boehringer Mannheim).

Results

BQ788 Induces Signs of Differentiation and Reduces the Viability of Human Melanoma Cells in Vitro To test the hypothesis that ETRB function plays a role in melanoma cell growth and differentiation, we cultured 7 human melanoma cell lines and one human kidney cell line with the selective ETRB antagonist, BQ788. Inspection of the treated cultures reveals drastic morphological changes in some of the melanoma lines. As shown in FIGS. 1A and B, SK-MEL 28 cells develop large cytoplasmic vacuoles and enhanced pigmentation. Similar changes are seen with antagonist treatment of A375 and RPMI 7951 cells (not shown). All the lines show increased surface area and most of them (except for SK-MEL 3) show major increases in pigmentation. Treatment of SK-MEL 5 cells also results in a dendritic phenotype, similar to that observed in normal, mature melanocytes (FIGS. 1C, D). In contrast, treatment of kidney 293 cells with BQ788 does not result in any of these morphological changes (FIGS. 1E, F).

In addition to inducing morphological changes indicating of differentiation, treatment of the melanoma cells with BQ788 eventually results in reduced cell number and cell death. This effect was quantified using the MTS assay. As shown in FIG. 2, all 7 melanoma lines tested show a very significant loss in the number of viable cells upon treatment with 100 $\mu$M BQ788, although some lines are clearly more sensitive than others. In contrast, the number of kidney cells is not reduced by high concentrations of BQ788, demonstrating that this inhibitor is not generally toxic.

To verify that the cells express ETRB, we performed RT-PCR using published primer sequences (Hamroun, et al., J. Cardiovasc, Pharmacol., 26(3):S156–8 (1995)). All of these cell lines, including the kidney cells, display a band of the size expected for authentic ETRB mRNA (FIG. 3A). Five additional PCR cycles were required to detect the band in RPMI 7951 cells. In addition, all cell lines express ETRA, at various levels (FIG. 3B). Similar findings on receptor expression in some of these lines have been reported previously (Yohn, et al., Biochem. Biophys. Res. Commun., 201:449–57 (1994); Ohtani, et al., Biochem. Biophys. Res. Commun., 234:526–30 (1997)).

The co-expression of ETRA allowed us to examine the effect of adding the selective ETRA antagonist BQ123 (Itoh, et al., Biochem. Biophys. Res. Commun., 195:969–75 (1993)) to these cells. As shown in FIG. 4, BQ123 does not reduce the number of viable cells in any of these cell lines, even at high concentrations. In fact, this antagonist slightly increases cell number in two of the melanoma lines, A375 and SK-MEL 28. Thus, the effects of BQ788 at high concentrations are not mediated through ETRA.

To further examine the effect of BQ788, we used the highly selective ETRB agonist, sarafotoxin 6c (S6c) (Takasaki, et al., Toxicon, 26:543–8 (1998)). As predicted, at concentrations of 0.1 to 1 $\mu$M, S6c increases A375 cell number (FIG. 5). Importantly for the present experiments, S6c can completely block the effects of BQ788 on A375 cells (FIG. 5). Thus, the ability of BQ788 to lower melanoma cell number is likely to be through its action on ETRB and not as a side effect on another aspect of melanoma cell physiology.

BQ788 Inhibits Human Melanoma Growth in Nude Mice

For the in vivo experiments we chose the A375 melanoma cell line. Although this line is not the most sensitive to BQ788 treatment in culture, it is known to grow readily in nude mice. First, dissociated cells were injected as a suspension into the flank of nude mice. When tumors developed, one mouse was sacrificed, the tumor removed and cut into pieces of approximately 3 mm in diameter and implanted under the skin of a new series of nude mice. When the tumor reaches 4 mm in diameter (which takes approximately 12 days, but can vary), 25 $\mu$l of a solution containing 20, $\mu$g/$\mu$l of BQ788 dissolved in 2% polyoxythylene (60) hydrogenated castor oil (HCO60) (Ishikawa, et al., Proc. Natl. Acad. Sci. USA, 91:4892–6 (1994)) was injected into the center of the tumor daily for 9 days. Tumors in control mice were injected in the same way with 25 $\mu$l of 2% HCO60. Before each injection the tumor dimensions were measured. Results from three experiments, using a total of 10 BQ788-treated mice and 8 vehicle-treated control mice are shown in FIG. 6. At the outset, the mean tumor volume was 26 mm³ in both control and BQ788-treated mice. After 9 days the mean tumor volume of the control group reached 376 mm³ while the treated group had a mean tumor volume of 84 mm³. Calculation of the growth rate (final size minus initial size) reveals that the BQ788-treated tumors grow 6 times slower compared to controls. Similar conclusions come from comparison of tumor weights (means of 446 mg versus 93 mg; p<0.005).

We next asked if systemic administration of BQ788 inhibits tumor growth. In these experiments, tumor induction and the starting point of the treatments were as for the intra-tumor approach. At that point, mice were injected i.p. with 100 μl of BQ788 solution (0.6 mg BQ788 in 30% water and 70% saline, at a final HCO60 concentration of 0.6%) once or twice a day for a period of 9 days. Control mice received the same injections but without BQ788. In the first experiment, mice were injected once a day, and in the second experiment the mice were injected in the morning and then again in the early evening. As results from these two experiments did not differ, they were pooled and are presented in FIG. 7A. It is clear that systemic administration also results in effective inhibition of tumor growth. However, there was some heterogeneity in the response of the mice to BQ788. For the first 6 days, tumors in the BQ788 grow did not differ significantly from their size at day 1. After 6 days, the BQ788 mice could be divided into two subgroups that responded differently to the drug, as shown in FIG. 7B. In one set of mice, BQ788 treatment slowed tumor growth while in the other set of mice, the tumors shrank and displayed complete growth arrest.

Several of the tumors from the i.p. injection experiment were taken for histological examination on day 10. Sections were stained with anti-CD31 antibody for angiogenesis, and with the TUNEL method for apoptosis. In general, BQ-788 treatment results in enhanced TUNEL labeling (FIG. 8), suggesting the drug increases apoptosis. Staining with the anti-CD-31 antibody to highlight blood vessels reveals no evidence that BQ788 blocks angiogenesis (data not shown). SK-MEL 3 displays increased surface area (dendritic morphology) in response to BQ788, while its viability is less affected than the other lines. The viability of SK-MEL 24 and SK-MEL 31 cells is more affected by BQ788, and they also display the additional morphological feature of increased pigmentation. SK-MEL 5 is similar to the latter two lines, but also shows increased dendricity. A375, SK-MEL 28 and the most sensitive cell line RPMI 7951, display vacuoles in their cytoplasm and an almost complete loss of viability in response to BQ788. These effects in culture appear mediated by the action of the drug on ETRB itself, as BQ788 is ineffective on A375 cells in the presence of the ETRB agonist S6c. A further indication of the specificity of the action of BQ788 is its very different effect on kidney 293 cells. Moreover, the ETRA selective blocker BQ123 did not inhibit melanoma cell growth in culture, even at high concentrations.

The cell line that shows the highest degree of sensitivity to treatment with BQ788, RPMI 7951, also displays lower levels of ETRB mRNA expression compared to the other cell lines used in this study. Human metastatic melanoma cells have been reported to display decreased ETRB expression compared to primary melanoma cells. Kikuchi et al., *Biochem. Biophys. Res. Commun.*, 219:734–9 (1996). Therefore, the data herein suggests that metastatic melanoma cells could be the most sensitive to treatment with BQ788.

The culture findings, particularly with lines RPMI 7951, SK-MEL 28 and A375, as well as the TUNEL results in vivo, indicate that the drug induces apoptosis. We also have evidence for a possible autocrine role since some of the lines express ET1 mRNA (data not shown). This idea is further supported by the growth stimulation observed upon addition of the ETRB-specific agonist to A375 cells (FIG. 5). The opposite results obtained with the selective ETRA antagonist BQ123 on A375 and SK-MEL 28 indicate that the A and B receptors mediate entirely different actions of ET on these cells. When ETRA is blocked, proliferation can be enhanced. Of note, the major ETRA transcript expressed by melanoma cell lines is truncated and lacks high affinity binding to ET. Zhang et al. (Zhang, et al., *Brit. J. Cancer*, 78:1141–6 (1998). In contrast, in normal tissues wild type ETRA is the predominant transcript.

Moreover, there is evidence that drugs comprising BQ788 can be well tolerated. Hashimoto, et al., *Biol. Pharamceut. Bull.*, 21:800–4 (1998); Haynes, et al., *Circulation*, 93:1860–70 (1996); Sütsch, et al., *Circulation*, 98:2262–8 (1998).

What is claimed is:

1. A method of treating cancer comprising: administering to an individual in need of treatment for cancer, a selective inhibitor of an endothelin-B receptor activity, in a therapeutically effective amount.

2. The method of claim 1 wherein said administering is systemic.

3. The method of claim 1 wherein said administering is to a tumor site.

4. The method of claim 1 wherein said cancer is skin cancer.

5. The method of claim 1 wherein said cancer is metastasizing.

6. The method of claim 1 wherein said cancer is prostate cancer.

7. The method of claim 1 wherein said cancer is ovarian cancer.

8. The method of claim 1 wherein said inhibitor is BQ788 or a derivative thereof.

9. The method of claim 1 wherein said inhibitor is an antisense molecule to an endothelin receptor-B nucleic acid or an endothelin receptor-B agonist nucleic acid.

10. A method for reducing abnormal proliferation of a cell comprising an endothelin B-receptor, said method comprising administering an inhibitor to an endothelin B-receptor to said cell in an amount for reducing proliferation.

11. The method of claim 10 wherein said cell is cancerous.

12. A method for inducing differentiation in a cell comprising an endothelin B-receptor, said method comprising administering an inhibitor to an endothelin B-receptor to said cell in an amount for inducing differentiation.

13. The method of claim 12 wherein said cell is cancerous.

14. A method for inducing apoptosis in a cell comprising an endothelin B-receptor, said method comprising administering an inhibitor to an endothelin B-receptor to said cell in an amount for inducing apoptosis.

15. The method of claim 14 wherein said cell is cancerous.

16. A method for delivering a substance to a cancerous cell in an individual comprising:

conjugating a substance to BQ788 or a derivative thereof which is functionally equivalent to form a conjugate; and administering said conjugate to said individual.

* * * * *